(12) United States Patent
De Troostembergh et al.

(10) Patent No.: US 9,845,483 B2
(45) Date of Patent: Dec. 19, 2017

(54) ALCOHOLIC FERMENTATION PROCESS IN THE PRESENCE OF A HIGH ALCOHOL TOLERANT YEAST AND A MALTOTRIOSE POSITIVE YEAST

(71) Applicant: Cargill, Incorporated, Wayzata, MN (US)

(72) Inventors: Jean-Claude Marie Pierre De Troostembergh, Tielt-Winge (BE); Bernhard Horbach, Krefeld (DE); Michael Josef Christian Kruse, Krefeld (DE); Nicolas Andre Albert Meurens, Chastra (BE)

(73) Assignee: CARGILL, INCORPORATED, Wayzata, MN (US)

( * ) Notice: Subject to any disclaimer, the term of this patent is extended or adjusted under 35 U.S.C. 154(b) by 224 days.

(21) Appl. No.: 14/403,699

(22) PCT Filed: May 31, 2013

(86) PCT No.: PCT/US2013/043539
§ 371 (c)(1),
(2) Date: Nov. 25, 2014

(87) PCT Pub. No.: WO2013/181496
PCT Pub. Date: Dec. 5, 2013

(65) Prior Publication Data
US 2015/0140629 A1    May 21, 2015

(30) Foreign Application Priority Data

May 31, 2012   (EP) .................................... 12004209

(51) Int. Cl.
*C12P 7/14*       (2006.01)
*C12C 12/00*      (2006.01)
*C12N 1/18*       (2006.01)

(52) U.S. Cl.
CPC .............. *C12P 7/14* (2013.01); *C12C 12/006* (2013.01); *C12N 1/18* (2013.01); *Y02E 50/17* (2013.01)

(58) Field of Classification Search
CPC ............ C12P 7/14; C12C 12/006; C12N 1/18
See application file for complete search history.

(56) References Cited

U.S. PATENT DOCUMENTS

| 5,716,653 A * | 2/1998 | Simard ................. A21D 8/047 426/429 |
| 2013/0330791 A1* | 12/2013 | Milos ...................... C12F 3/10 435/136 |

FOREIGN PATENT DOCUMENTS

DE        253 044 A1    1/1988

OTHER PUBLICATIONS

Mukhtar et al., Comparative study on two commercial strains of *Saccharomyces cerevisiae* for optimum ethanol production on industrial scale, Journal of Biomedicine and Biotechnology, 2010, p. 1-5.*
Linko et al., Continuous ethanol production by immobilized yeast reactor, Biotechnology Letters, vol. 3, 1981, p. 21-26.*
DD253044 translated document.*
International Search Report, PCT/US2013/043539, dated Jul. 5, 2013, 3 pgs.
John Londesborough: "Fermentation of Maltotriose by Brewer's and Baker's Yest", Biotechnology Letters, vol. 23, 2001, pp. 1995-2000, XP002685300.

* cited by examiner

*Primary Examiner* — Taeyoon Kim
*Assistant Examiner* — Tiffany Gough

(57) ABSTRACT

The invention relates to an alcoholic fermentation process in the presence of one or more high alcohol tolerant yeast and one or more maltotriose positive yeast. The process of the present invention can be a fermentation process for the production of ethanol, for the production of beer, for the production of wine and the like. in a preferred embodiment, the present invention relates to a process for the production of ethanol in the presence of distiller's yeast and baker's yeast.

13 Claims, No Drawings

ALCOHOLIC FERMENTATION PROCESS IN THE PRESENCE OF A HIGH ALCOHOL TOLERANT YEAST AND A MALTOTRIOSE POSITIVE YEAST

CROSS REFERENCE TO RELATED APPLICATION

This application is a national phase application of International Application PCT/US2013/043539, filed May 31, 2013, entitled ALCOHOLIC FERMENTATION PROCESS IN THE PRESENCE OF A HIGH ALCOHOL TOLERANT YEAST AND A MALTOTRIOSE POSITIVE YEAST, which claims the benefit of the European Provisional Patent Application, Serial No. 12004209.8, filed May 31, 2012, entitled ALCOHOLIC FERMENTATION PROCESS IN THE PRESENCE OF A HIGH ALCOHOL TOLERANT YEAST AND A MALTOTRIOSE POSITIVE YEAST, which are hereby incorporated by reference in their entirety.

FIELD OF THE INVENTION

The invention relates to an alcoholic fermentation process in the presence of one or more high alcohol tolerant yeasts and one or more maltotriose positive yeasts.

BACKGROUND OF THE INVENTION

Ethanol is a 2-carbon alcohol with the molecular formula $CH_3CH_2OH$. It is an important industrial product nowadays and its importance is increasing. Ethanol can be produced by a chemical process or via biological processes, by fermentation of glucose containing substrate by yeast. The latter is often referred to as bioethanol. For ease of reading, in the present description ethanol is understood to be bioethanol, unless otherwise specified.

Ethanol finds different industrial applications. Firstly, it is used in the food and beverage industry. Ethanol can either be produced 'in situ' during fermentation processes like brewing and wine production or be produced as an end product of a fermentation process and subsequently added to beverages in order to produce alcoholised beverages. This ethanol is referred to as potable ethanol. Secondly, ethanol is increasingly used as an alternative energy source for fossil fuels. This ethanol is referred to as fuel ethanol or biofuel. It is less purified than potable ethanol but the production process is largely similar.

In some parts of the world, the use of raw materials for producing fuel ethanol puts the use of the same raw materials for food production under a lot of pressure. Also for this reason, it is important to increase the yield of current ethanol production processes.

Nowadays, production of ethanol as an end product uses yeast strains known as distiller's yeast. Some research work has been done in the field to develop yeast strains having increased alcohol tolerance, in order to increase the yield of ethanol production process. It is also known to use other yeast strains having a high alcohol tolerance, i.e. able to produce high amounts of ethanol, such as brewer's yeast.

DD253044A1 discloses the use of distiller's yeast and brewer's yeast in the production of ethanol.

There is an ever existing demand from industry to provide a process with increased yield and increased rate of ethanol production, without increased production costs. The present invention provides such a solution.

SUMMARY OF THE INVENTION

The present invention relates to an alcoholic fermentation process comprising fermenting a carbohydrate containing substrate in the presence of one or more high alcohol tolerant yeasts having an alcohol tolerance of at least 100 g/l and one or more maltotriose positive yeasts.

Further, the present invention relates to a use of one or more high alcohol tolerant yeasts and one or more maltotriose positive yeasts in an alcoholic fermentation process.

Further, the present invention relates to a composition for use in an alcoholic fermentation process, characterized in that said composition comprises one or more high alcohol tolerant yeasts and one or more maltotriose positive yeasts.

Further, the present invention relates to a composition comprising one or more high alcohol tolerant yeasts and one or more maltotriose positive yeasts, characterized in that said composition is a by-product of the alcoholic fermentation process according to the first aspect of the present invention.

DETAILED DESCRIPTION

The term "about", as used herein when referring to a measurable value is meant to encompass variations of 5%, 4%, 3%, 2%, 0.5% or even 0.1% of the specified value.

The present invention relates to an alcoholic fermentation process comprising fermenting a carbohydrate containing substrate in the presence of one or more high alcohol tolerant yeasts having an alcohol tolerance of at least 100 g/l and one or more maltotriose positive yeasts.

Fermentation Process

Alcoholic fermentation is a process wherein yeast converts glucose, or maltose and some yeasts maltotriose, from a suitable fermentable carbohydrate containing substrate into ethanol and carbon dioxide. Thus an alcoholic fermentation process for the purpose of the present invention is a process for the production of ethanol. Such process can be for example a process for ethanol production, beer production, and wine production. In a preferred embodiment, the process is a process for the production of ethanol wherein ethanol is the final product.

A fermentation process for the production of ethanol can be carried out either as a direct saccharification process or as a simultaneous saccharification and fermentation process (SSF process). Preferably, the process of the present invention is a SSF process.

Traditionally, the method for the production of ethanol, typically from cereals, is the so-called direct saccharification process. In this process, saccharification of the mash is done prior to fermentation. The steps in a conventional direct saccharification process, where the raw material comprises starch, include:

Liquefaction or dextrinization: conversion of the starch to dextrins by addition of an alpha-amylase enzyme to the mash, by which the mash is turned into a so-called 'liquefied mash';

Full saccharification: conversion of the maltodextrins in the liquefied mash to glucose by addition of an amyloglucosidase or glucoamylase enzyme, by which the liquefied mash is turned into a 'fully saccharified mash'. This is preferably done at optimal conditions of pH and temperature for the enzyme used, as known in the art and/or indicated by enzyme producers.

Fermentation: pitching of the fully saccharified mash (i.e. inoculation of the fermentation medium) with yeast, conversion of the glucose and maltose in the fully saccharified mash into ethanol and carbon dioxide through the action of a suitable yeast for the production of ethanol, such as distiller's yeast. The fully saccharified mash is turned into a fermented mash.

Nowadays, most often, alcoholic fermentation for the production of ethanol is as a SSF process. In such SSF process, at least part of the saccharification step and the fermentation step are done simultaneously instead of in subsequent steps.

For the purpose of the present invention, the saccharification step and the fermentation steps can be done in separate, subsequent steps. Preferably, for the purpose of the present invention, the whole saccharification step and the whole fermentation step are done simultaneously. After liquefaction, as described above, the 'liquefied mash' is cooled down to fermentation temperature (from about 20 to about 50° C.). One or more amyloglucosidase or glucoamylase enzymes are added, the pH is adjusted to the optimal value for the glucoamylase (pH typically around 4.5) and at the same time, pitching of the mash is done so that fermentation can begin.

Alternatively, part of the saccharification step is done simultaneously with the fermentation step. In this case, saccharification of the liquefied mash is done until a certain amount of the mash is converted to glucose and pitching of the fermentation medium is done before full saccharification is obtained, such that part of the saccharification takes place at the same time as fermentation.

The fermentation process of the present invention can be a batch, a fed batch or a continuous process. Supplying the substrate and/or the yeast can thus be batch, fed batch or continuous.

In a SSF process, the fermentable sugars released by the glucoamylase are directly consumed by the yeast. Typically in SSF, a concentration of 20 g/l or more, preferably 30 g/l or more, more preferably 40 g/l or more, even more preferably 50 g/l or more, and most preferably 60 g/l or more of maltose is measured in the mash, while it is typically close to zero in a fully saccharified mash where substantially all maltose has been converted into glucose. The use of maltose by yeast requires the presence of two proteins: a permease of maltose that enables the entrance of the sugar in the yeast cell and an intra-cellular maltase that cleaves maltose into two molecules of glucose. Maltose is thus a significant sugar in a SSF process regulation because it is not only a substrate for the glucoamylase in saccharification, but also for the yeast in fermentation. Consequently, a yeast strain that is able to consume maltose in presence of glucose ferments faster in SSF process. Preferably even, a yeast strain able to consume maltose faster is advantageous in the process of the present invention. This is the case of the baker's yeast, which is also able to consume maltotriose. Typically for baker's yeast, maltotriose can be present in the medium in an amount of from 20 to 40 g/l.

Typically, in an alcoholic fermentation process, yeast is added to a fermentation medium comprising a suitable, fermentable carbohydrate-containing substrate. The one or more high alcohol tolerant yeast can be added separately and/or subsequently to the one or more maltotriose positive yeast, or vice versa. It is also possible to add both types of yeasts simultaneously. Further it is also possible to mix the yeasts first, and then use the mixture, rehydrated if needed, for pitching. Mixing of the yeasts can be achieved for example by simple blending, especially when dried yeasts are used. The fermentation medium typically has a dry substance of from 10% by weight (wt. %) to 50 wt. %, more preferably of from 15 wt. % to 40 wt. % even more preferably of from 20 wt. % to 35 wt. %. The fermentation is carried out at temperatures in the range of from 20° C. to 50° C., more preferably of from 25° C. to 45° C., even more preferably of from 30° C. to 40° C. At the end of the fermentation process the yeast is deactivated for example by temperature and the final product is recovered by any suitable method known in the art. If the end product is ethanol, it can be recovered by distillation for example.

Yeast

During alcoholic fermentation, yeast converts glucose from a suitable, fermentable carbohydrate-containing substrate into ethanol and carbon dioxide. Different yeasts are used for different purposes, depending on their characteristics.

Yeasts are characterized among other things by their alcohol tolerance, i.e. the level of alcohol in the medium above which the yeast starts to die. Several yeasts with a high alcohol tolerance have been selected and developed over the years, and are typically used for the purpose of producing ethanol. Typical examples of such yeasts are: brewer's yeast, distiller's yeast, wine yeast. High alcohol tolerant yeasts typically have an alcohol tolerance of above 100 g of alcohol per liter of the medium wherein the yeast is comprised (g alcohol/l medium). Other yeasts have a lower alcohol tolerance, and are therefore typically not used for the purpose of producing ethanol because of the low efficiency and productivity the process would have. Low alcohol tolerant yeasts typically have an alcohol tolerance of 100 g alcohol/l or below. An example of such yeast is baker's yeast.

Yeasts are further characterized by their ability to grow on maltotriose, due to the presence of a gene. Maltotriose is a trisaccharide, composed of three molecules of glucose linked with $\alpha$-1,4 glycosidic bonds (Degree of polymerisation 3, DP3). Yeast that is able to grow on maltotriose (i.e. on a medium having only maltotriose as source of carbohydrate), thus able to ferment maltotriose into ethanol, is maltotriose positive. Yeast that is not able to grow on a medium having only maltotriose as source of carbohydrate, is maltotriose negative, i.e. not able to ferment maltotriose into ethanol.

Most yeasts are able to convert maltose (DP2) into ethanol and carbon dioxide. However, certain yeast strains have been specifically developed over the years for their ability to rapidly convert maltose and also to convert maltose even in the presence of glucose.

High alcohol tolerant yeasts comprise distiller's yeast, brewer's yeast and wine yeast. Distiller's yeast for example is characterized by an alcohol tolerance of around 110-120 g alcohol/l. Further, it is advantageuous in the process of the present invention that the high alcohol tolerant yeast is maltotriose negative. Distiller's yeast for example is maltotriose negative. Further, distiller's yeast for example has a preference to use free glucose (DP1) instead of maltose (DP2) when both are present; such that the yeast will use maltose only once it has used substantially all available free glucose. Distiller's yeast can be from the species *Saccharomyces cerevisiae*. Preferably natural, non-GMO yeasts are used for the purpose of the present invention. Thus for the purpose of the present invention, the high alcohol tolerant yeast can be distiller's yeast, brewer's yeast, wine yeast or a combination of two or more thereof.

Maltotriose positive yeasts comprise baker's yeast. Baker's yeast is thus able to produce ethanol when grown on maltotriose. Baker's yeast is further characterized in that it is a low alcohol tolerant yeast, it has an alcohol tolerance of around 90-100 g alcohol/l. It has no preference in using glucose or maltose as substrate. Baker's yeast is also characterized in that it can use maltose more rapidly than other yeasts. Baker's yeast can be from the species *Saccharomyces cerevisiae*. Preferably natural, non-GMO yeasts are used for the purpose of the present invention. The maltotriose positive yeast for the purpose of the present invention thus preferably also has a low alcohol tolerance and preferably is also able to consume maltose rapidly. For example, baker's yeast can use maltose more rapidly than distiller's yeast.

Now, it has surprisingly been found by the inventors of the present invention that the combined use of one or more high alcohol tolerant yeasts, with one or more maltotriose positive yeasts during the fermentation process of the present invention is unexpectedly and advantageously influencing the production of ethanol, preferably in SSF process. In comparison to the use of one or more high alcohol tolerant yeast only, such as distiller's yeast, the use of both high alcohol tolerant yeast and maltotriose positive yeast significantly increases the yield of ethanol, it increases the rate of ethanol production, i.e. the productivity of the process, and it increases the onset of fermentation, i.e. fermentation will start more rapidly.

When both type of yeasts are used in the process of the present invention, a synergetic effect occurs whereby the production yield and the rate of ethanol production is increased. It is believed that the high alcohol tolerance of the high alcohol tolerant yeast enables it to continue fermentation when the ethanol concentration in the medium (i.e. ethanol titer) is too high for the maltotriose positive yeast. At the earlier stage of fermentation, while the high alcohol tolerant yeast converts the free glucose, the maltotriose positive yeast's ability to convert maltose (DP2) and maltotriose (DP3) at the same time is responsible for a higher speed of fermentation and a higher yield of the process. Through the high yield and higher speed, less by-products, such as isomaltose, which is not fermentable by yeast, are formed during the fermentation process. Yield increase, preferably the yield increase in SSF process, can be as high as from about 2 to about 6, 10, 11, 12, 13, 14, 15% increase compared to a similar fermentation process where only high alcohol tolerant yeast is used.

Preferably for the purpose of the present invention, the one or more high alcohol tolerant yeast comprises distiller's yeast, more preferably, the one or more high alcohol tolerant yeast is distiller's yeast.

Further preferably for the purpose of the present invention, the one or more maltotriose positive yeast is low alcohol tolerant.

Further preferably for the purpose of the present invention, the one or more maltotriose positive yeast comprises baker's yeast, more preferably, the one or more maltotriose positive yeast is baker's yeast.

Thus preferably, the fermentation process of the present invention is a fermentation process for the production of ethanol, in the presence of distiller's yeast and baker's yeast.

Preferably, the one or more high alcohol tolerant yeast comprises brewer's yeast and the one or more maltotriose positive yeast comprises baker's yeast. In a further preferred embodiment, the one or more high alcohol tolerant yeast is brewer's yeast and the one or more maltotriose positive yeast is baker's yeast.

The minimum amount of total yeast, i.e. high alcohol tolerant yeast plus maltotriose positive yeast in the fermentation medium can be as low as 0.005% by weight (wt %) of the fermentation medium. However, it will influence the speed of fermentation, and preferably the amount of total yeast is from 0.1 wt % to 5 wt % on the fermentation medium.

Preferably, the ratio high alcohol tolerant yeast to maltotriose positive yeast, i.e. the ratio active high alcohol tolerant yeast to active maltotriose positive yeast, is from 20:80 to 80:20, preferably from 25:75 to 75:25, more preferably from 30:70 to 70:30, even more preferably form 40:60 to 60:40, yet even more preferably from 45:55 to 55:45. Most preferably, the ratio high alcohol tolerant yeast to maltotriose positive yeast is about 50:50.

The yeasts can be used in any suitable form such as for example fresh yeast, active dried yeast, which can be rehydrated before use or instant dried yeast, which does not need rehydration before use and can be used as is. However if one of the applied yeast is taken in a certain form, it is convenient to take the other yeast in the same form. If one chooses to take yeasts of different forms, care should be taken to make sure the ratio active yeast is respected. Thus in the present invention, ratio of yeasts means the concentration of active yeast of one type to active yeast of the other type.

Fermentable Substrate

Yeast converts glucose into alcohol and carbon dioxide. Any substrate that is a source of glucose that can be made available to the yeast is a suitable substrate for the purpose of the present invention. Preferably, the substrate comprises maltose and more preferably also comprises maltotriose. Such substrate can be derived from cereals such as wheat, corn, barley oat, rye, rice; from potato, fruits, fruit waste, wood pulp and such biomasses that can be fermented by yeast. The preferred substrate however is derived from starch, such as a partially hydrolysed starch. Starch can be from any source, such as cereals, fruits like banana, plant roots like cassava or potato, pea and the like. Preferably, the starch is from one or more cereals. The one or more cereal can be wheat, corn, barley, oat, rye, rice and the like. In one preferred embodiment, the cereal comprises wheat. In a most preferred embodiment, the cereal is wheat. Any type of wheat can be used, such as hard wheat, soft wheat, high and low amylose containing varieties and genetically modified varieties thereof.

A partial hydrolysed starch can be obtained by any method known in the art, such as a liquefaction step as described above.

Preferably, the process of the present invention further comprises the steps of recovering the ethanol and the whole stillage. Thus preferably, the SSF process further comprises the steps of:

Distillation: separation of ethanol from the aqueous phase. The remaining slurry consisting of aqueous phase and solids is called 'whole stillage'. The resulting ethanol fraction can be further dehydrated to remove residual water, or otherwise further refined.

Centrifugation: separation of the whole stillage into a solid fraction, called 'distillers wet grains', and a soluble fraction, called 'thin stillage'.

Evaporation: concentration of the thin stillage to obtain a so-called 'condensed thin stillage' or 'condensed distillers solubles'.

Drying: drying of the distillers wet grains to obtain 'distillers dried grain' or drying of a mixture of distillers wet grains and condensed distillers solubles to obtain 'distillers dried grains and solubles'.

The whole stillage and all products derived from it, such as distillers wet grains, thin stillage, condensed thin stillage, distillers dried grain, distillers dried grains and soluble are thus by-products of the fermentation process of the present invention. These by-products can be used as is or can be further treated and used as animal feed, some of them can be burned to recover heat energy.

A further advantage of the present invention is that the fermentation is more complete such that less residual sugars remain in the whole stillage and thus in all products derived from it. This is advantageous because there is less risk of lactic fermentation during storage of the whole stillage or any products derived from it. Thus the process of the present invention has a positive impact on the stabilisation of the whole stillage and any products derived from it. Also, if the whole stillage or any products derived from it, are used in animal feed application, the lower amount of residual sugar in the feed can be beneficial for the health of the animal. Further, the whole stillage or any products derived from it contain extracts from the one or more high alcohol tolerant yeast and from the one or more maltotriose positive yeast used for fermentation and which have been deactivated/destroyed during distillation or during other treatment step causing the deactivation of the yeast. Thereby, the whole stillage or any products derived from it contain beneficial nutrients such as vitamins, yeast protein and the like, which are beneficial for the health of the animal fed with the whole stillage or any products derived from it.

Thus further, the present invention relates to a composition comprising high alcohol tolerant yeast and maltotriose positive yeast and/or high alcohol tolerant yeast and maltotriose positive yeast extracts characterized in that said composition is a by-product of the fermentation process. Such by-product can be the whole stillage or any product derived from it, such as such as distillers wet grains, thin stillage, condensed thin stillage, distillers dried grain, distillers dried grains and soluble.

Further, the present invention relates to a feed composition comprising the whole stillage or any products derived from it, obtainable by the process of the present invention.

Further, the present invention relates to a use of one or more high alcohol tolerant yeasts and one or more maltotriose positive yeasts in a process for the production of ethanol. The one or more high alcohol tolerant yeast can be added separately and/or subsequently to the one or more maltotriose positive yeast, or vice versa. It is also possible to add both types of yeasts simultaneously. Further it is also possible to mix the yeasts first, and then use the mixture, rehydrated if needed, for pitching. Mixing of the yeasts can be achieved for example by simple blending, especially when dried yeasts are used.

Further, the present invention relates to a composition for use in a process for the production of ethanol, characterized in that said composition comprises one or more high alcohol tolerant yeast and one or more maltotriose positive yeast. The composition can comprise high alcohol tolerant yeast and maltotriose positive yeast, i.e. active high alcohol tolerant yeast and active maltotriose positive yeast, in a ratio of from 20:80 to 80:20, preferably from 25:75 to 75:25, more preferably from 30:70 to 70:30, even more preferably form 40:60 to 60:40, yet even more preferably from 45:55 to 55:45. Most preferably, the ratio high alcohol tolerant yeast to maltotriose positive yeast is about 50:50. The composition can comprise fresh yeast, active dried yeast or instant dried yeast, whatever form of yeast is suitable. Preferably, the composition comprises active dried yeast. Additionally to the two types of yeast, the composition can further comprise vitamins, minerals, salts and the like.

EXAMPLES

The present invention will be illustrated with the following examples.

Example 1

Wheat mash at 33.0% dry substance is used. 90 w/w % of the total dry substance of the mash is liquefied starch.

The mash has following composition:

TABLE 1 composition of wheat mash

| Glucose (g/l) | DP2 (g/l) | DP3 (g/l) |
| --- | --- | --- |
| 25.2 | 71.5 | 39.8 |

The pH of the mash is adjusted from 5.0 to 4.5 with concentrated sulphuric acid. The glucoamylase Deltazym LE-5 is added at dosage 0.05% on dry substance and the viscosity reducing enzyme Shearzyme plus is added at dosage 0.02% on dry substance.

Part of the wheat mash is subjected to saccharification, at 60° C. for 24 hours, to determine the fermentable content. After saccharification, the wheat mash has the following composition:

TABLE 2 composition of wheat mash after complete saccharification

| Glucose (g/l) | DP2 (g/l) | DP3 (g/l) |
| --- | --- | --- |
| 255.7 | 12.3 | 10.7 |

The rest of the wheat mash is used for the trial. Saccharification is done simultaneously to fermentation.

Active dried distiller's yeast (Thermosacc from Lallemand) "T" and active dried baker's yeast (from Bruggeman) "B" are rehydrated separately in demineralised water for 30 minutes at room temperature (20° C.) at a dilution factor 6.

A 2-liter fermenter is filled with 1 liter of working volume. Pitching of fermentation medium is then done with 50 ml of hydrated yeast. Several trials are made:

Pitching with 50 ml of hydrated distiller's yeast

Pitching with 50 ml of hydrated baker's yeast

Pitching with 50 ml of a 50:50 (v:v) mix of hydrated distiller's yeast and hydrated baker's yeast Pitching with 50 ml of a 25:75 (v:v) mix of hydrated distiller's yeast and hydrated baker's yeast.

Each trial is done in duplicate. Fermentations are carried on at 32° C. and agitation at 200 rpm. Samples are taken after 48 and 72 hours of fermentation.

The composition of the beers after 48 hours of fermentation is given in table 3.

TABLE 3 composition of the beers after 48 hours of fermentation

| Ratio T-B | Glucose (g/l) | DP2 (g/l) | DP3 (g/l) | Ethanol (g/l) | Glycerol (g/l) | Ethanol yield (%) |
| --- | --- | --- | --- | --- | --- | --- |
| 0:100 | 50.5 | 7.7 | 10.0 | 95.6 | 7.1 | 68.5 |
| 25:75 | 23.6 | 7.0 | 10.2 | 106.9 | 7.4 | 76.5 |
| 50:50 | 18.4 | 7.0 | 10.7 | 108.7 | 7.5 | 77.8 |
| 100:0 | 26.2 | 16.2 | 10.9 | 94.8 | 7.0 | 67.9 |

The composition of the beers after 72 hours fermentation is given in table 4. The residual glucose in the 100% Bruggeman culture and ethanol were still at similar value than the ones after 48 hours of fermentation. The 50:50 mix reaching 119.5 g/l was more productive than the 75:25 mix.

TABLE 4 composition of the beers after 72 hours of fermentation

| Ratio T-B | Glucose (g/l) | DP2 (g/l) | DP3 (g/l) | Ethanol (g/l) | Glycerol (g/l) | Ethanol yield (%) |
|---|---|---|---|---|---|---|
| 0:100 | 53.8 | 7.5 | 8.3 | 96.0 | 7.0 | 68.7 |
| 25:75 | 10.4 | 6.2 | 7.6 | 116.3 | 7.6 | 83.2 |
| 50:50 | 5.4 | 5.3 | 7.5 | 119.5 | 7.6 | 85.5 |
| 100:0 | 17.9 | 6.5 | 10.1 | 111.0 | 7.6 | 79.4 |

Example 2

Wheat mash at 33.0% dry substance is used. 90 w/w % of the total dry substance of the mash is liquefied starch.

The mash has following composition:

TABLE 1 composition of wheat mash

| Glucose (g/l) | DP2 (g/l) | DP3 (g/l) |
|---|---|---|
| 25.2 | 71.5 | 39.8 |

The pH of the mash is adjusted from 5.0 to 4.5 with concentrated sulphuric acid. The glucoamylase Deltazym LE-5 is added at dosage 0.05% on dry substance and the viscosity reducing enzyme Shearzyme plus is added at dosage 0.02% on dry substance.

Part of the wheat mash is subjected to saccharification, at 60° C. for 24 hours, to determine the fermentable content. After saccharification, the wheat mash has the following composition:

TABLE 2 composition of wheat mash after complete saccharification

| Glucose (g/l) | DP2 (g/l) | DP3 (g/l) |
|---|---|---|
| 248.5 | 11.6 | 10.4 |

The rest of the mash is used for the trial. Saccharification is done simultaneously to fermentation.

Active dried distiller's yeast (Ethanol Red) "ER" and active dried baker's yeast (Saf Instant Red) "SR" are rehydrated separately in demineralised water for 30 minutes at room temperature (20° C.) at a dilution factor 6.

A 2-liter fermenter is filled with 1 liter of working volume. Pitching of fermentation medium is then done with 50 ml of hydrated yeast. Several trials are made:

Pitching with 50 ml of hydrated distiller's yeast

Pitching with 50 ml of hydrated baker's yeast

Pitching with 50 ml of a 50:50 (v:v) mix of hydrated distiller's yeast and hydrated baker's yeast Pitching with 50 ml of a 25:75 (v:v) mix of hydrated distiller's yeast and hydrated baker's yeast.

Each trial is done in duplicate. Fermentations are carried on at 32° C. and agitation at 200 rpm. Samples are taken after 24 and 72 hours of fermentation.

The composition of the beers after 24 hours of fermentation is given in table 3.

TABLE 3 composition of the beers after 24 hours of fermentation

| Ratio ER-SR | Glucose (g/l) | DP2 (g/l) | DP3 (g/l) | Ethanol (g/l) | Glycerol (g/l) | Ethanol production rate (g/l/h) |
|---|---|---|---|---|---|---|
| 0:100 | 31.4 | 29.3 | 7.7 | 83.1 | 6.8 | 3.5 |
| 25:75 | 29.2 | 16.9 | 7.8 | 91.5 | 7.1 | 3.8 |
| 50:50 | 34.8 | 18.6 | 7.9 | 88.2 | 7.0 | 3.7 |
| 100:0 | 35.0 | 45.3 | 7.6 | 71.4 | 6.3 | 3.0 |

The composition of the beers after 72 hours fermentation is given in table 4. The residual glucose in the 100% SR culture is very high, indicating that the fermentation was stuck. It confirmed that the ethanol tolerance of the baker's yeast SR is lower than the one of the distiller's yeast ER. The 50:50 mix reaching 130.9 g/l of ethanol was more productive than the 75:25 mix, reaching 127.8 g/l of ethanol.

TABLE 4 composition of the beers after 72 hours of fermentation

| Ratio ER-SR | Glucose (g/l) | DP2 (g/l) | DP3 (g/l) | Ethanol (g/l) | Glycerol (g/l) | Ethanol yield (%) |
|---|---|---|---|---|---|---|
| 0:100 | 42.5 | 6.7 | 6.7 | 109.0 | 7.5 | 75.9 |
| 25:75 | 6.7 | 5.6 | 5.8 | 127.8 | 8.2 | 89.1 |
| 50:50 | 5.2 | 4.8 | 5.5 | 130.9 | 8.2 | 91.2 |
| 100:0 | 7.3 | 5.7 | 6.7 | 127.1 | 7.8 | 88.6 |

Example 3

Comparative Example

Wheat mash at 28% dry substance is used. 90 w/w % of the total dry substance is liquefied starch. The mash has following composition:

TABLE 1 composition of wheat mash

| Glucose (g/l) | DP2 (g/l) | DP3 (g/l) |
|---|---|---|
| 20.1 | 42.6 | 32.8 |

The pH of the mash is adjusted from 5.0 to 4.5 with concentrated sulphuric acid. The glucoamylase Deltazym LE-5 is added at dosage 0.05% on dry substance and the viscosity reducing enzyme Shearzyme plus is added at dosage 0.02% on dry substance.

Part of the wheat mash is subjected to saccharification, at 60° C. for 24 hours, to determine the fermentable content. After saccharification, the wheat mash has the following composition:

TABLE 2 composition of wheat mash after complete saccharification

| Glucose (g/l) | DP2 (g/l) | DP3 (g/l) |
|---|---|---|
| 210.0 | 13.3 | 6.8 |

The rest of the mash is used for the trial. Saccharification is done simultaneously to fermentation.

Active dried distiller's yeast (Thermosacc from Lallemand) "T" and active dried brewer's yeast (CBC-1 from Lallemand) "C" are rehydrated separately in demineralised water for 30 minutes at room temperature (20° C.) at a dilution factor 6.

A 2-liter fermenter is filled with 1 liter of working volume. Pitching of fermentation medium is then done with 10 ml of hydrated yeast:

Pitching with 10 ml of a 50:50 (v:v) mix of hydrated distiller's yeast and hydrated brewer's yeast The trial is done in duplicate. Fermentation is carried on at 32° C. and agitation at 200 rpm. Samples are taken after 24 and 72 hours of fermentation.

In another trial the combination of the distiller's yeast with a maltotriose positive yeast is tested. Active dried distiller's yeast (Thermosacc from Lallemand) "T" and active maltotriose positive yeast (Superstart from Lallemand) "S" are rehydrated separately in demineralised water for 30 minutes at room temperature (20° C.) at a dilution factor 6.

A 2-liter fermenter is filled with 1 liter of working volume. Pitching of fermentation medium is then done with 10 ml of hydrated yeast:

Pitching with 10 ml of a 50:50 (v:v) mix of hydrated distiller's yeast and hydrated maltotriose positive yeast The trial is done in duplicate. Fermentation is carried on at 32° C. and agitation at 200 rpm. Samples are taken after 24 and 72 hours of fermentation.

The composition of the beers after 24 hours of fermentation is given in table 3.

TABLE 3 composition of the beers after 24 hours of fermentation

| Ratio 50:50 | Glucose (g/l) | DP2 (g/l) | DP3 (g/l) | Ethanol (g/l) | Glycerol (g/l) |
|---|---|---|---|---|---|
| T:C | 17.1 | 50.3 | 5.8 | 56.1 | 5.0 |
| T:S | 15.7 | 22.5 | 5.7 | 72.2 | 5.7 |

After 24 hours already the amount of ethanol in the beers is much higher for the mixture distiller's yeast with maltotriose positive yeast compared to the mixture distiller's yeast with typical brewer's yeast.

The composition of the beers after 72 hours fermentation is given in table 4.

TABLE 4 composition of the beers after 72 hours of fermentation

| 50:50 | Glucose (g/l) | DP2 (g/l) | DP3 (g/l) | Ethanol (g/l) | Glycerol (g/l) | Ethanol yield (%) |
|---|---|---|---|---|---|---|
| T:C | 2.5 | 6.5 | 5.5 | 104.0 | 6.6 | 94.9 |
| T:S | 1.6 | 5.4 | 3.7 | 106.6 | 6.8 | 97.2 |

The invention claimed is:

1. A process for the production of ethanol comprising fermenting a carbohydrate containing substrate in the presence of one or more high alcohol tolerant yeasts having an alcohol tolerance of at least 100 g/l and one or more maltotriose positive yeasts, wherein the substrate comprises maltose and maltotriose.

2. The process of claim 1, further comprising the steps of recovering ethanol and recovering whole stillage.

3. The process of claim 1, wherein the one or more high alcohol tolerant yeast is maltotriose negative and/or wherein the one or more maltotriose positive yeasts is low alcohol tolerant.

4. The process of claim 1, wherein the one or more maltotriose positive yeasts has the ability to ferment maltose faster than the high alcohol tolerant yeast.

5. The process of claim 1, wherein the one or more high alcohol tolerant yeasts is distiller's yeast.

6. The process of claim 1, wherein the one or more high alcohol tolerant yeasts is brewer's yeast.

7. The process of claim 1, wherein the one or more maltotriose positive yeasts comprises baker's yeast.

8. The process of claim 1, wherein the substrate comprises maltose and maltotriose.

9. The process of claim 1, wherein the ratio of high alcohol tolerant yeast to maltotriose positive yeast is 75:25 to 25:75.

10. The process of claim 1, wherein the ratio of high alcohol tolerant yeast to low alcohol tolerant yeast is about 50:50.

11. The process of claim 1, characterized in that it is a simultaneous saccharification and fermentation process.

12. The process of claim 1 wherein the process is a process for making beer.

13. The process claim 1, wherein the substrate is derived from starch.

* * * * *